US009216267B2

(12) United States Patent
Spandorfer et al.

(10) Patent No.: US 9,216,267 B2
(45) Date of Patent: *Dec. 22, 2015

(54) COMPACT SELF-CONTAINED AUTOMATED MDI ADAPTERS OR UNITS FOR VENTILATORS

(71) Applicant: iDTx Systems, Inc., North Charleston, SC (US)

(72) Inventors: Michael Spandorfer, Charleston, SC (US); Murphy Pearce Gilbert, Charleston, SC (US)

(73) Assignee: IDTX SYSTEMS, INC., North Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/523,403

(22) Filed: Oct. 24, 2014

(65) Prior Publication Data

US 2015/0040899 A1    Feb. 12, 2015

Related U.S. Application Data

(63) Continuation of application No. 13/110,436, filed on May 18, 2011, now Pat. No. 8,869,793.

(60) Provisional application No. 61/345,730, filed on May 18, 2010.

(51) Int. Cl.
*A61M 11/00* (2006.01)
*A61M 16/08* (2006.01)
(Continued)

(52) U.S. Cl.
CPC ............ *A61M 16/0816* (2013.01); *A61B 5/082* (2013.01); *A61B 5/4836* (2013.01);
(Continued)

(58) Field of Classification Search
CPC ................ A61M 16/0051; A61M 2016/0027; A61M 15/009; A61M 2205/583; A61M 2016/0036; A61M 16/0816; A61M 16/0003; A61M 16/0883; A61M 16/0057; A61M 2016/003; A61M 2205/3334; A61M 2205/3592; A61M 2205/6072; A61M 2209/01; A61M 16/1045; A61M 16/14; A61M 2016/0021; A61M 2205/14; A61M 2205/276; A61M 2205/3368; A61M 2205/3561; A61M 2205/3569; A61M 2205/505; A61M 2205/52; A61M 2205/6009; A61M 2205/6054; A61M 2205/609; A61M 2205/8206; A61M 2230/43; A61M 15/0003; A61M 15/0005; A61M 15/0066; A61M 15/008; A61M 15/0081; A61M 15/083; A61B 5/082; A61B 5/4836
USPC .................. 128/203.14, 205.23, 202.27, 910
See application file for complete search history.

(56) References Cited

U.S. PATENT DOCUMENTS 4,558,710 A    12/1985    Eichler
4,604,093 A    8/1986    Brown et al.
(Continued)

FOREIGN PATENT DOCUMENTS

GB    2 055 046 A    2/1981
WO    WO 98/31413 A1    7/1998

OTHER PUBLICATIONS

Carrillo et al., The Development of an Automatic Metered Dose Inhaler, Vanderbilt University Department of BioMedical Engineering, 32 pages, Apr. 27, 2004.
(Continued)

*Primary Examiner* — Steven Douglas
(74) *Attorney, Agent, or Firm* — Myers Bigel Sibley & Sajovec, PA

(57) ABSTRACT

A system for providing automated delivery of medication to a ventilator circuit that extends between a mechanical ventilator and a patient includes a connector that resides in-line with a portion of the ventilator circuit, a portable medication delivery unit attached to the connector, and a control device in communication with the portable delivery unit. The portable delivery unit includes a housing releasably holding at least one metered dose inhaler canister containing medication and an actuator held by the housing and in communication with the canister to direct the canister to release medication to the ventilator circuit for the patient. The control device is configured to control an amount and/or frequency of medication delivery from the canister to the ventilator circuit for a respective patient and to direct the actuator to actuate to deliver the medication from the canister to the ventilator circuit at a defined amount and/or frequency.

17 Claims, 7 Drawing Sheets

(51) Int. Cl.

| | | |
|---|---|---|
| A61M 16/00 | (2006.01) | |
| A61M 15/00 | (2006.01) | |
| A61M 16/14 | (2006.01) | |
| A61B 5/08 | (2006.01) | |
| A61B 5/00 | (2006.01) | |
| A61M 16/10 | (2006.01) | |

(52) U.S. Cl.
CPC ......... *A61M15/0003* (2014.02); *A61M 15/008* (2014.02); *A61M 15/009* (2013.01); *A61M 15/0066* (2014.02); *A61M 15/0081* (2014.02); *A61M 16/0003* (2014.02); *A61M 16/0051* (2013.01); *A61M 16/0057* (2013.01); *A61M 16/0883* (2014.02); *A61M 16/14* (2013.01); *A61M 15/0005* (2014.02); *A61M 15/0083* (2014.02); *A61M 16/1045* (2013.01); *A61M 2016/003* (2013.01); *A61M 2016/0021* (2013.01); *A61M 2016/0027* (2013.01); *A61M 2016/0036* (2013.01); *A61M 2205/14* (2013.01); *A61M 2205/276* (2013.01); *A61M 2205/3334* (2013.01); *A61M 2205/3368* (2013.01); *A61M 2205/3561* (2013.01); *A61M 2205/3569* (2013.01); *A61M 2205/3592* (2013.01); *A61M 2205/505* (2013.01); *A61M 2205/52* (2013.01); *A61M 2205/609* (2013.01); *A61M 2205/6009* (2013.01); *A61M 2205/6054* (2013.01); *A61M 2205/6072* (2013.01); *A61M 2205/8206* (2013.01); *A61M 2209/01* (2013.01); *A61M 2230/43* (2013.01)

(56) References Cited

U.S. PATENT DOCUMENTS

| | | |
|---|---|---|
| 4,819,629 A | 4/1989 | Jonson |
| 4,934,358 A | 6/1990 | Nilsson et al. |
| 4,984,158 A | 1/1991 | Hillsman |
| 5,002,048 A | 3/1991 | Makiej, Jr. |
| 5,020,527 A | 6/1991 | Dessertine |
| 5,103,814 A | 4/1992 | Maher |
| 5,178,138 A | 1/1993 | Walstrom et al. |
| 5,277,175 A | 1/1994 | Riggs et al. |
| 5,284,133 A | 2/1994 | Burns et al. |
| 5,297,543 A | 3/1994 | Larson et al. |
| 5,363,842 A | 11/1994 | Mishelevich et al. |
| 5,392,768 A | 2/1995 | Johansson et al. |
| 5,394,866 A | 3/1995 | Ritson et al. |
| 5,404,871 A | 4/1995 | Goodman et al. |
| 5,431,154 A | 7/1995 | Seigel et al. |
| 5,437,267 A | 8/1995 | Weinstein et al. |
| 5,438,982 A | 8/1995 | MacIntyre |
| 5,474,058 A | 12/1995 | Lix |
| 5,497,764 A | 3/1996 | Ritson et al. |
| 5,507,277 A | 4/1996 | Rubsamen et al. |
| 5,520,166 A | 5/1996 | Ritson et al. |
| 5,522,378 A | 6/1996 | Ritson et al. |
| 5,522,385 A | 6/1996 | Lloyd et al. |
| 5,542,410 A | 8/1996 | Goodman et al. |
| 5,544,647 A | 8/1996 | Jewett et al. |
| 5,560,353 A | 10/1996 | Willemot et al. |
| 5,564,414 A | 10/1996 | Walker et al. |
| 5,608,647 A | 3/1997 | Rubsamen et al. |
| 5,617,844 A | 4/1997 | King |
| 5,622,162 A | 4/1997 | Johansson et al. |
| 5,622,163 A | 4/1997 | Jewett et al. |
| 5,655,516 A | 8/1997 | Goodman et al. |
| 5,676,129 A | 10/1997 | Rocci, Jr. et al. |
| 5,694,919 A | 12/1997 | Rubsamen et al. |
| 5,724,957 A | 3/1998 | Rubsamen et al. |
| 5,743,252 A | 4/1998 | Rubsamen et al. |
| 5,755,218 A | 5/1998 | Johansson et al. |
| 5,770,585 A | 6/1998 | Kaufman et al. |
| 5,794,612 A | 8/1998 | Wachter et al. |
| 5,809,997 A | 9/1998 | Wolf |
| 5,826,570 A | 10/1998 | Goodman et al. |
| 5,881,716 A | 3/1999 | Wirch et al. |
| 5,967,141 A | 10/1999 | Heinonen |
| 6,012,450 A | 1/2000 | Rubsamen |
| 6,014,972 A | 1/2000 | Sladek |
| 6,079,413 A | 6/2000 | Baran |
| 6,116,234 A | 9/2000 | Genova et al. |
| 6,119,684 A | 9/2000 | Nöhl et al. |
| 6,123,068 A | 9/2000 | Lloyd et al. |
| 6,138,669 A | 10/2000 | Rocci, Jr. et al. |
| 6,148,815 A | 11/2000 | Wolf |
| 6,202,642 B1 | 3/2001 | McKinnon et al. |
| 6,223,744 B1 | 5/2001 | Garon |
| 6,237,597 B1 | 5/2001 | Kovac |
| 6,260,549 B1 | 7/2001 | Sosiak |
| 6,318,361 B1 | 11/2001 | Sosiak |
| 6,325,062 B1 | 12/2001 | Sosiak |
| 6,358,058 B1 | 3/2002 | Strupat et al. |
| 6,390,088 B1 | 5/2002 | Nöhl et al. |
| 6,435,175 B1 | 8/2002 | Stenzler |
| 6,523,536 B2 | 2/2003 | Fugelsang et al. |
| 6,529,446 B1 | 3/2003 | de la Huerga |
| 6,557,552 B1 | 5/2003 | Cox et al. |
| 6,595,389 B2 | 7/2003 | Fuchs |
| 6,598,602 B1 | 7/2003 | Sjoholm |
| 6,615,825 B2 | 9/2003 | Stenzler |
| 6,631,716 B1 | 10/2003 | Robinson et al. |
| 6,651,844 B2 | 11/2003 | Tomaka et al. |
| 6,681,767 B1 | 1/2004 | Patton et al. |
| 6,684,880 B2 | 2/2004 | Trueba |
| 6,725,859 B1 | 4/2004 | Rothenberg et al. |
| 6,830,046 B2 | 12/2004 | Blakley et al. |
| 6,871,645 B2 | 3/2005 | Wartman et al. |
| 6,962,152 B1 | 11/2005 | Sladek |
| 7,191,777 B2 | 3/2007 | Brand et al. |
| 7,198,044 B2 | 4/2007 | Trueba |
| 7,201,166 B2 | 4/2007 | Blaise et al. |
| 7,201,167 B2 | 4/2007 | Fink et al. |
| 7,347,200 B2 | 3/2008 | Jones et al. |
| 7,495,546 B2 | 2/2009 | Lintell |
| 7,549,421 B2 | 6/2009 | Levi et al. |
| 7,600,511 B2 | 10/2009 | Power et al. |
| 7,634,995 B2 | 12/2009 | Grychowski et al. |
| 7,748,382 B2 | 7/2010 | Denyer et al. |
| 7,905,230 B2 | 3/2011 | Schuler et al. |
| 8,151,794 B2 | 4/2012 | Meyer et al. |
| 2002/0069869 A1 | 6/2002 | Farmer |
| 2002/0069870 A1 | 6/2002 | Farmer |
| 2003/0200964 A1 | 10/2003 | Blakley et al. |
| 2004/0069301 A1 | 4/2004 | Bacon |
| 2004/0084050 A1 | 5/2004 | Baran |
| 2004/0107961 A1 | 6/2004 | Trueba |
| 2004/0138577 A1 | 7/2004 | Kline |
| 2004/0255936 A1 | 12/2004 | Urbanus |
| 2005/0039746 A1 | 2/2005 | Grychowski et al. |
| 2005/0139211 A1 | 6/2005 | Alston et al. |
| 2005/0183725 A1 | 8/2005 | Gumaste et al. |
| 2005/0235987 A1 | 10/2005 | Smaldone et al. |
| 2005/0268908 A1 | 12/2005 | Bonney et al. |
| 2005/0274378 A1 | 12/2005 | Bonney et al. |
| 2006/0021614 A1 | 2/2006 | Wermeling et al. |
| 2006/0254581 A1 | 11/2006 | Genova et al. |
| 2007/0151560 A1 | 7/2007 | Price et al. |
| 2007/0173731 A1 | 7/2007 | Meka et al. |
| 2008/0009761 A1 | 1/2008 | Acker et al. |
| 2008/0308101 A1 | 12/2008 | Spandorfer |
| 2009/0120431 A1* | 5/2009 | Borgschulte et al. .... 128/200.23 |
| 2009/0137920 A1 | 5/2009 | Colman et al. |

OTHER PUBLICATIONS

Carrillo et al., Automated Metered Dose Inhaler Presentation #5, Vanderbilt University Department of Engineering, 11 pages, dated Apr. 7, 2004.

(56) References Cited

OTHER PUBLICATIONS

Ohmeda Project: Automated Metered-Dose Inhaler Deliver Device, Biomedical Engineering Design Projects, College of Engineering University of Wisconsin-Madison, printed from http://homepages.cae.wisc.edu/, printed Jul. 3, 2008, 4 pages, final poster presentation and demo stated to be date May 10, 2002.

European Office Action Corresponding to European Patent Application No. 08770987.9; Dated: Feb. 28, 2014; 10 Pages.

Product Specification and Directions, Metered Dose Inhaler (MDI) Adapter, Instrumentation Industries, Inc., 2 pages, (Date of first publication unknown but for exam purposes only, is to be considered before the priority date of the instant application.).

Ari et al., A Guide to Aerosol Delivery Devices for Respiratory Therapists, $2^{nd}$ Edition, American Association for Respiratory Care, © 2009, Exemplary pp. 22, 24 and 34.

International Search Report and Written Opinion for corresponding PCT Application No. PCT/US2008/066883, Date of mailing Oct. 1, 2008.

* cited by examiner

COMPACT SELF-CONTAINED AUTOMATED MDI ADAPTERS OR UNITS FOR VENTILATORS

RELATED APPLICATIONS

This application is a continuation of U.S. application Ser. No. 13/110,436, filed May 18, 2011, which claims priority from U.S. Provisional Application No. 61/345,730, filed May 18, 2010, the disclosures of which are hereby incorporated herein in their entireties.

FIELD OF THE INVENTION

This invention relates to ventilators and to drug delivery systems.

BACKGROUND

Mechanical ventilation is a method of mechanically assisting or replacing spontaneous breathing when patients cannot do so. One type of ventilation system employs the use of an endotracheal or tracheostomy tube secured into a patient's upper respiratory tract. Gas is mechanically delivered to the patient via the tube. In many cases, mechanical ventilation is used in acute settings such as an intensive care unit for a short period of time during a serious illness. Currently, the main form of mechanical ventilation is positive pressure ventilation, which works by increasing the pressure in the patient's airway and thus forcing additional air into the lungs. To aid in the treatment of ventilated patients, aerosol medicines are aspirated in situ through an access point in the ventilator system. This process is manual, requiring the medical professional to deliver the aerosols on a regular basis.

Automatically administering medication to mechanically ventilated patients may reduce healthcare costs and improve patient safety.

SUMMARY

According to some embodiments, a portable control unit for providing automated delivery of medication to a ventilator circuit that extends between a mechanical ventilator and a patient includes: a housing configured to releasably hold at least one inhaler containing medication, wherein the inhaler is in fluid communication with the ventilator circuit; an actuator held by the housing and in communication with the inhaler to direct the inhaler to release medication to the ventilator circuit for a respective patient; a controller configured to control an amount and/or frequency of medication delivery from the inhaler to the ventilator circuit for a respective patient and to actuate the actuator to deliver medication from the inhaler to the ventilator circuit at a defined amount and/or frequency; and a display held by the housing for displaying parameters including the defined amount and/or frequency of medication delivery and an amount of medication remaining in the inhaler, wherein the controller is configured to dynamically update the displayed parameters.

The unit may include a user interface held by the housing to allow an operator to input to the controller the amount and/or frequency of medication delivery from the inhaler to the ventilator circuit for a respective patient. The unit may include a caregiver-initiated manual override control in communication with the controller to direct the actuator to deliver medication from the inhaler to the ventilator circuit for a respective patient irrespective of the defined amount and/or frequency of medication delivery. The unit may include a patient-initiated manual override control in communication with the controller to direct the actuator to deliver medication from the inhaler to the ventilator circuit for a respective patient irrespective of the defined amount and/or frequency of medication delivery. The unit may include an agitator held by the housing and in communication with the controller and inhaler to agitate the inhaler prior to actuation of the actuator to deliver medication from the inhaler to the ventilator circuit.

In some embodiments, the unit is in combination with a connector that forms a portion of the ventilator circuit and includes an entry port to receive a nozzle of the inhaler therethrough such that medication is delivered from the inhaler to an interior of the connector when the actuator is actuated. A gas flow sensor is disposed in the interior of the connector, with the gas flow sensor configured to detect a gas flow direction through the connector and communicate the gas flow direction to the controller. The controller may be configured to actuate the actuator when the gas flow direction in the connector is from the ventilator to the patient based on data detected by the gas flow sensor. The gas flow sensor may be configured to detect at least one gas flow characteristic of gas flowing through the connector and to communicate the detected at least one gas flow characteristic to the controller, with the controller configured to adjust the amount and/or frequency of medication delivery in response to the detected at least one gas flow characteristic. In some embodiments, the portable control unit is a compact and/or lightweight device that attaches to the connector.

In some embodiments, the controller is configured to: (i) lock the unit to prevent actuation of the actuator and prevent unwanted adjustment of operational parameters; (ii) receive identification information associated with an operator of the unit; (iii) verify that the operator is an authorized user based on the identification information; and (iv) unlock the unit in response to verification that the operator is an authorized user. In some embodiments, the controller is configured to: (i) lock the unit to prevent actuation of the actuator and prevent unwanted adjustment of operational parameters; (ii) receive identification information associated with a patient; (iii) verify that the patient is to receive the medication contained in the inhaler based on the identification information; and (iv) unlock the unit in response to verification that the patient is to receive the medication contained in the inhaler.

In further embodiments, a system for providing automated delivery of medication to a ventilator circuit that extends between a mechanical ventilator and a patient includes a connector that resides in-line with a portion of the ventilator circuit and a compact and/or lightweight portable control unit attached to the connector. The portable control unit includes: a housing configured to releasably hold at least one inhaler containing medication, wherein the inhaler includes an outlet nozzle received through an entry port in the connector such that the inhaler is in fluid communication with the ventilator circuit; an actuator held by the housing and in communication with the inhaler to direct the inhaler to release medication to the ventilator circuit for a respective patient; and a controller configured to control an amount and/or frequency of medication delivery from the inhaler to the ventilator circuit for a respective patient and to actuate the actuator to deliver the medication from the inhaler to the ventilator circuit at a defined amount and/or frequency.

The unit may include a user interface held by the housing to allow an operator to input to the controller the amount and/or frequency of medication delivery from the inhaler to the ventilator circuit for a respective patient. The unit may include a manual override control in communication with the controller to direct the actuator to actuate to deliver medication from the inhaler to the ventilator circuit for a respective patient irrespective of the defined amount and/or frequency of medication delivery.

In some embodiments, the system includes a gas flow sensor disposed in the connector, with the gas flow sensor configured to detect a gas flow direction through the connector and communicate the gas flow direction to the controller, wherein the controller is configured to actuate the actuator in response to the gas flow sensor detecting a gas flow direction from the ventilator to the patient. The gas flow sensor may be configured to detect at least one gas flow characteristic of gas flowing through the connector and to communicate the detected gas flow characteristic to the controller, with the controller configured to adjust the amount and/or frequency of medication delivery in response to the detected at least one gas flow characteristic. The unit may include a display for displaying parameters including the defined amount and/or frequency of medication delivery and an amount of medication remaining in the inhaler, wherein the controller is configured to dynamically update the displayed parameters.

In further embodiments, a diagnostic system for use with a ventilator circuit that runs between a mechanical ventilator and a patient includes: a first housing configured to releasably hold a container containing particles to be inhaled by the patient, wherein the container is in fluid communication with the ventilator circuit; a first actuator at least partially in the first housing and in communication with the container to deliver particles to be inhaled by the patient from the container to the ventilator circuit; an exhaled gas measurement sensor disposed in the ventilator circuit configured to perform a measurement on gas exhaled from the patient after the particles have been inhaled by the patient; and at least one controller configured to actuate the first actuator to deliver the particles to be inhaled by the patient from the container to the ventilator circuit, to receive the measurement on gas subsequently exhaled by the patient from the exhaled gas measurement sensor, and to determine a current state or condition of the patient in response to the received measurement.

The system may further include a portable unit for providing automated delivery of medication to the ventilator circuit, with the unit including: a second housing configured to releasably hold an inhaler containing medication, wherein the inhaler is in fluid communication with the ventilator circuit; and a second actuator held by the second housing and in communication with the inhaler to direct the inhaler to release medication to the ventilator circuit for the patient. The at least one controller is configured to: (i) control an amount and/or frequency of medication delivery from the inhaler to the ventilator circuit for the patient; (ii) actuate the second actuator to deliver the medication from the inhaler to the ventilator circuit at a defined amount and/or frequency; and (iii) adjust the defined amount and/or frequency of medication delivery in response to the determined current state or condition of the patient.

The system may include a display for displaying information including at least one of the defined amount of medication delivery and/or frequency of medication delivery, an amount of medication remaining in the inhaler, and the determined state or condition of the patient, wherein the controller dynamically updates the displayed information.

In further embodiments, a connector for use with a ventilator circuit that runs between a mechanical ventilator and a patient for evenly releasing medication from an inhaler into the ventilator circuit includes: an outer fluid channel in fluid communication with the inhaler and configured to contain medication from the inhaler therein; an inner fluid channel radially spaced-apart from and in fluid communication with the outer fluid channel, wherein the inner fluid channel forms a portion of the ventilator circuit; a wall separating the outer fluid channel and the inner fluid channel; and a plurality of perforations in the wall. When gas flows through the ventilator circuit in a direction from the ventilator to the patient, medication contained in the outer fluid channel is released through the perforations, into the inner fluid channel, and into the gas in the ventilator circuit to the patient.

The connector may be in combination with a controller and a gas flow sensor disposed in the ventilator circuit configured to detect a gas flow direction through the ventilator circuit and communicate the gas flow direction to the controller. The controller is configured to actuate the inhaler to release medication therefrom to the outer fluid channel after detection by the gas flow sensor of a gas flow direction from the patient to the ventilator and before detection by the gas flow sensor of a gas flow direction from the ventilator to the patient.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

Figure 1:
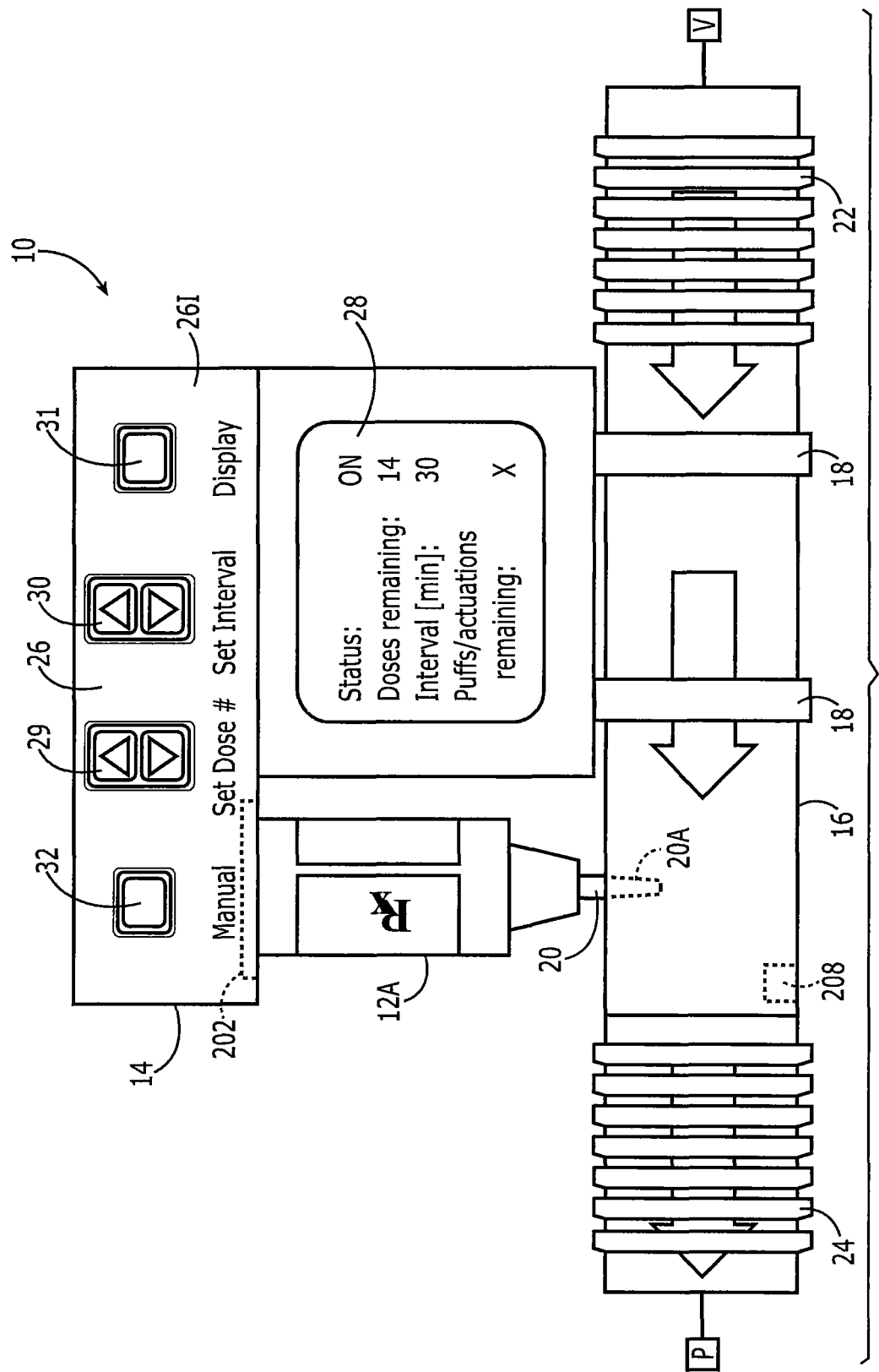
FIG. 1 is a schematic illustration of an automated medication and control delivery unit according to some embodiments.

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout.

Thicknesses and dimensions of some components may be exaggerated for clarity. Broken lines illustrate elements or features not visible from the presented view (e.g., on the opposite side) or as an optional element unless otherwise indicated. It will be understood that when an element is referred to as being "attached," "connected," or "coupled" to another element, it can be directly connected or coupled to the other element or intervening elements may be present. In contrast, when an element is referred to as being "directly attached," "directly connected," or "directly coupled" to another element, there are no intervening elements present. Also, although a feature is described with respect to one embodiment, this feature may be used with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

Turning now to the figures, an automated medication control and delivery unit 10 is illustrated in FIG. 1. The unit 10 can be used to provide controlled and automated delivery of an inhalable substance (e.g., medication) to a ventilator circuit 11. The unit 10 can be a compact self-contained device. The unit 10 can be a low-cost, standalone unit that is easy to install and operate. In some embodiments, the unit 10 weighs between about 2 ounces and about 5 pounds. In some embodiments, the unit 10 weighs between about 2 ounces and about 16 ounces. In some embodiments, the unit 10 has a volume of between about 16 cubic inches and about 64 cubic inches. As will be described in more detail below, the unit 10 may be relatively compact and lightweight for suitable connection to the ventilator circuit 11 or a connector associated therewith.

As illustrated, the unit 10 is configured to receive a metered dose inhaler (MDI) device 12A, such as a pressurized MDI (pMDI) or Dry Powder Inhaler (DPI). The unit 10 includes a housing 14. The MDI 12A may be snugly and releasably held by the housing 14 or by components within the housing 14.

The unit 10 may include a sensor 201 (FIG. 5), such as a proximity sensor (Hall-effect, optical, and the like) to detect whether the MDI 12A has been properly installed.

Also illustrated is a connector 16 that forms a part of the ventilator flow circuit 11. In some embodiments, the connector 16 is integrated with the unit 10 (i.e., the connector 16 is fixably attached to the unit 10, and can therefore be considered part of the unit 10). The connector 16 can be a tubular component with substantially the same diameter as the proximate portions of the ventilator circuit 11. In some embodiments, and as illustrated, the connector 16 is releasably attached to the unit 10. For example, the unit 10 may include one or more brackets or holders 18. The holders 18 may comprise straps, fingers, or other holders. The holders 18 may adjustably surround the connector 16 so as to releasably attach the connector 16 to the unit 10. In this regard, the connector 16 may be disposable although the unit 10 may be used multiple times for different patients. Other configurations to releasably attach the connector 16 to the unit 10 are envisioned. As described above, the unit 10 may be compact and lightweight. This configuration may facilitate connection to and disconnection from the connector 16. Also, the lightweight nature of the unit 10 may inhibit or prevent deflection or indentation of the connector 16 when attached thereto, and may also inhibit or prevent deflection of the connector 16 relative to the remainder of the ventilator circuit 11 (e.g., downward deflection in FIG. 1). Thus, the lightweight design may inhibit or prevent damage to the connector 16 (e.g., crushing or indentation) and may allow for a more consistent flow path through the ventilator circuit 11 and the connector 16 (e.g., a substantially straight flow path having a substantially even cross-section). Attaching and detaching the unit 10 to the connector 16 may allowed for a self-contained unit in a convenient location that performs the functions described below.

The MDI 12A includes a nozzle 20 with an exit port 20A (e.g., nozzle). The MDI 12A is positioned such that at least a portion of the exit port 20A is positioned inside the connector 16. The connector 16 may include an entry port to sealably receive the MDI 12A nozzle 20 (or the exit port 20A). For example, the connector 16 can directly or indirectly engage the nozzle 20 and/or the port 20A. In some embodiments, a raised collar (not shown) from the connector 16 can receive the MDI exit port 20A and/or provide resistance against an actuator (described in more detail below). In other embodiments, the connector 16 can include an entry port, and an extension, such as an angled elbow tube (not shown), can be fixably or releasably attached to the entry port. In any event, medication can be released from the MDI 12A to the interior of the connector 16, and therefore through the ventilator flow circuit 11, as will be described in more detail below.

Still referring to FIG. 1, the connector 16 includes first and second end segments 22, 24. The connector 16 connects with the ventilator flow circuit 11 leading to the ventilator V and the patient P. More particularly, the connector 16 connects with the ventilator flow circuit 11 leading to the ventilator V at or adjacent the first end segment 22 and the connector 16 connects with the ventilator flow circuit 11 leading to the patient P at or adjacent the second end segment 24. At least the first and second end segments 22, 24 may be axially and/or transversely flexible, may be an "accordion-like" conduit or corrugated tube, may have a telescoping form, or a combination of the same. These flexible configurations can allow the connector 16 to more easily and securely connect to the remainder of the ventilator flow circuit 11. For example, the end segments 22, 24 may allow for some movement of the ventilator flow circuit 11 (e.g., at the patient and/or ventilator end) without compromising the sealed or tight connections to the connector 16.

An actuator 202 in communication with an upper end of the MDI 12A can automatically actuate the MDI 12A to release medication therefrom. The actuator 202 can provide motion to open a valve of the MDI 12A such that the MDI 12A dispenses a metered dose of medication through the exit port 20A and into the interior of the connector 16. In some embodiments, the actuator 202 takes the form of a plunger positioned above the MDI. In some embodiments, the actuator 202 can be similar to the actuators described in co-pending U.S. Patent Application Publication No. 2008/0308101, filed Jun. 13, 2008, the contents of which are incorporated by reference as if disclosed herein in its entirety.

Figure 5:
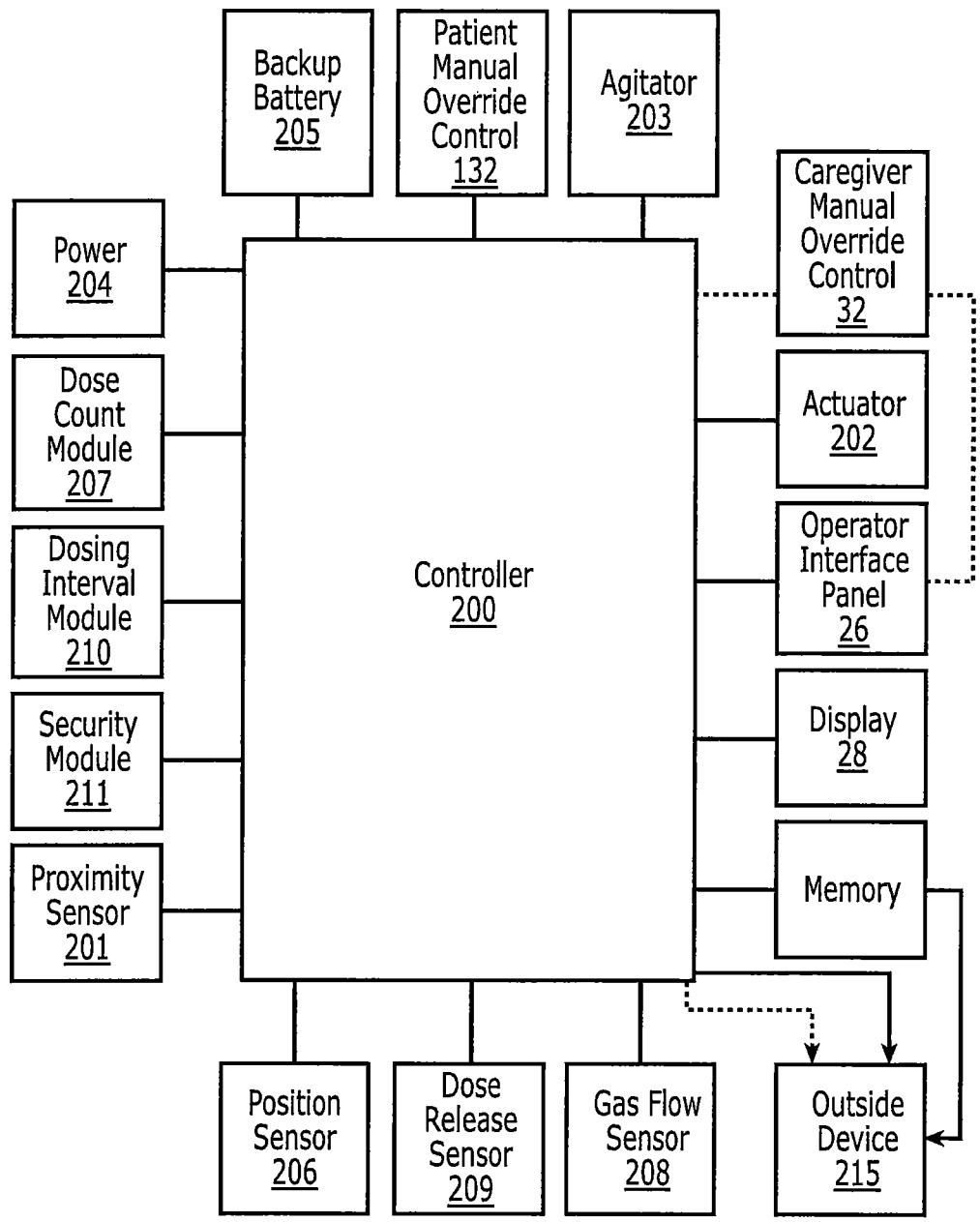
FIG. 5 is a block diagram illustrating a controller and other components that may be associated with automated medication and control delivery units according to some embodiments.

The unit 10 may include an agitator 203 (FIG. 5). For example, the agitator 203 may be included in the housing 14 and may contact the MDI 12A. Many medications should be agitated before delivery from the MDI 12A. The agitator 203 can shake or vibrate the MDI 12A in one or more directions. For example, the agitator 203 may shake the MDI back-and-forth in a vertical direction and/or a horizontal direction and/or in any other direction. In some embodiments, the agitator 203 can comprise a piezoelectric crystal or ceramic transducer.

The unit 10 typically includes an on-board microprocessor or controller 200 (FIG. 5) contained in the housing 14. The controller 200 may be operatively connected to and/or control, for example, an operator interface panel 26, a display 28, the actuator 202, and the agitator 203. The controller 200 may be operatively connected to and/or control other components and operations of the unit 10, as will be described in more detail below.

As illustrated in FIG. 1, the operator interface panel 26 includes a user interface (UI) 261 with a plurality of user controls. An operator can control the number of doses to be supplied from the MDI 12A via the UI control 29. The operator can also control the frequency of the supplied doses via the UI control 30. Thus, these controls allow the unit 10 to be programmed to selectively provide a desired, adjustable and automated delivery of medication to a respective patient from the MDI 12A to the connector 16 and therefore to the ventilator flow circuit. The operator interface panel 26 may also include a display UI control 31 and a manual override UI control 32, which will be described in more detail below. It is noted that the UI controls could be various input devices such as GUIs, electronic pull-down menus, buttons, wheels, or the like. Moreover, the operator interface panel 26 can be integrated with the display 28, which can be a GUI touch screen display with icons or other features providing the user input, for example.

The unit 10 is configured to display certain information and operational parameters on the display 28. For example, the doses remaining (i.e., the number of doses input by the operator or the number of doses associated with the MDI 12A less the number of doses already administered) may be displayed. The number of doses need not necessarily match the number of actuations as a patient may need more than one "puff per dose." In some embodiments, the unit 10 can be configured to track and/or display the number of actuations or "puffs." MDIs are sometimes prepackaged and pre-measured with a defined number of actuations or puffs (e.g., 60 to 400 actuations or puffs). Because the number of puffs per dose may vary based on a patient and/or a physician's orders, the unit can track the actuations or puffs to provide information and audible, visual or other warning as to when the MDI canister 12A will be empty or should be replaced. It is noted that although the unit 10 can track or measure actuations (puffs), the unit can also be programmed such that this information is converted to doses for a particular patient.

The interval between doses may also be displayed on the display 28. Other information such as the "status" of the MDI 12A can also be displayed. For example, the status may read "on" when the MDI is operating under an automated mode with defined programmed parameters or "off" if the MDI is not in an automated mode. The status may also inform the operator whether the MDI has been installed correctly and/or whether the MDI is operational in general. The controller 200 (FIG. 5) can continuously or at various times dynamically update the various information and parameters on the display 28 based on user input and/or based on the operation of the unit 10.

In some embodiments, all operational information can be displayed on the display 28 together. Alternatively, the information may scroll along the display 28 and/or the display 28 may toggle between different screens containing different information. The display UI control 31 may allow the operator to manually perform these scrolling and toggling operations. The display UI control 31 may also power the display 28 "on" and "off" in some embodiments. The display 28 may power "on" and "off" at various intervals for a power-saving mode. An "on" display mode may be triggered by a proximity sensor or by a clinician's manual input or at selected or pre-set time intervals. The display 28 may automatically operate prior to actuation and just after then go into power-saving mode.

Power may be provided to the unit 10 via a medical grade AC or DC power supply 204 (FIG. 5). The unit 10 may include a battery 205 (FIG. 5) to allow the unit 10 to function if the AC or DC power supply is interrupted. Alternatively, the power may be provided by an on-board battery 204 (FIG. 5) and the unit 10 can include one or more backup batteries 205 (FIG. 5). It is contemplated that various components could be powered by different power sources. For example, the actuator 202 and display 28 may be powered by different power sources.

In operation, the controller 200 (FIG. 5) can direct the agitator 203 to agitate the MDI 12A just prior to actuation and delivery of the medication from the MDI 12A based on the selected delivery frequency. The controller 200 can then direct the actuator 203 to actuate the MDI 12A to dispense medication into the ventilator flow circuit 11. The controller 200 typically times the actuation such that the medication is dispensed while the flow of gas through the connector 16 is toward the patient (i.e., while the patient inhales). This flow direction is indicated by the arrows in FIG. 1.

A position sensor 206 (FIG. 5) may be associated with the actuator 202 and/or with the MDI 12A such that movement of these components can be monitored. Thus, if the actuation of the MDI 12A is downward, the position sensor 206 may detect the delivery of a dose or puff based on downward movement. The position sensor 206 may also sense that the MDI 12A has returned to its proper position based on upward movement. The position sensor 206 may communicate with the controller 200 to provide information to the display 28 (for example, the "doses remaining" or "puffs/actuations remaining" count may be decremented).

Alternatively, a counter (e.g., dose count module 207, FIG. 5) associated with the actuator 202 can "count" the number of actuations. It is noted that two or more successive actuations could equal one dose where the dose is two or more "puffs" and the dose counter can indicate the number of doses remaining. As described above, the number of puffs can also be displayed and/or monitored. Because the rate at which puffs will be delivered may be programmed, the unit 10 can further calculate, monitor and/or display the time at which the MDI canister 12A will be empty. For example, the display 28 could show the number of puffs remaining, and how many hours and minutes remain before the canister is empty (or the date and/or time at which the canister will be empty).

The controller of the unit 10 can be in communication with the connector 16 or components therein. For example, there may be a gas flow sensor 208 disposed in the connector 16 (or elsewhere in the ventilator circuit 11) to detect incoming air from the ventilator V and exhaled breath from the patient P. In other words, the gas flow sensor 208 can measure or sense the direction of the flow of gas through the connector 16 (or the ventilator circuit 11) and communicate the same to the controller. As described above, the release of medication from the MDI 12A is timed so that the medication flows with the gas toward the patient. The gas flow sensor 208 may further verify that the medication properly reaches the patient and may communicate the same to the controller.

The gas flow sensor 208, or an additional sensor, may be used to measure pressure and/or the rate of change of pressure in the ventilator flow circuit, and may measure other gas flow characteristics such as volumetric gas flow rate and temperature, that indicate the patient's ability to receive the medication. The gas flow sensor 208 can measure ventilator flow circuit conditions and patient airway resistance, which may be used to determine the need for additional medication dosing and timing or modulation of the current specified dosing and timing of the medication. Higher pressure and/or a relatively short cycle time on reversal of gas flow may indicate that the ability of the patient to consume the medication through the lungs is impaired. In such case, the controller 200 may increase the dosage frequency or dosage amount to the patient or both. The adjustment may occur manually or automatically by an algorithm utilized by the controller 200. Similarly, to wean the patient, the frequency and/or dose amount can be reduced when patient airway resistance improves.

The unit 10 may comprise a dose release sensor 209 (FIG. 5). This sensor may verify that a dose of medication was actually dispensed and delivered. Verification may be provided and recorded in the controller 200 (e.g., in a database) or in another computer or memory storage device. Similarly, data from other sensors as disclosed herein may be collected and stored in the controller (e.g., in a database) or in another computer or memory storage device.

The sensors described herein and other sensors may perform other functions as described in co-pending U.S. Patent Application Publication No. 2008/0308101, filed Jun. 13, 2008, the disclosure of which is incorporated by reference as if disclosed herein in its entirety. Moreover, the unit 10 and/or the connector 16 may include any other components described in the co-pending application and incorporated by reference herein.

The unit 10 typically includes a manual override UI control 32. The operator may use this control to deliver an unscheduled release of medication, such as if the respiratory condition of the patient appears poor or upon an order from the doctor. The counter on the display (e.g., "doses or puffs remaining") will generally be decremented following use of the manual override.

The unit 10 may include other features. For example, the unit 10 may have a shutoff control to immediately cease the automated functions of the unit 10 (for example, in an emergency situation). The shutoff control may be part of the operator interface panel 26 or may be a separate switch on the unit 10.

The unit 10 may also provide alarms for various events, such as when the unit 10 is malfunctioning (e.g., one or more components have stopped operating) or when the MDI 12A is depleted of medication or approaching this state. The alarms may be visible alarms on the display 28 and/or audible alarms. The alarms may be sent to one or more of a PDA, cell phone, notepad, or other device carried by a clinician such as a nurse and/or a monitoring station.

The unit 10 may include certain features to enhance security and patient safety. For example, the operator may need to enter a password prior to operating the unit 10. The password may be entered via UI controls on the operator interface panel 26, for example. The unit 10 may also include or communicate with one or more identification devices and can include one or more optical or electronic devices. For example, the operator may be required to enter (e.g., swipe) or scan a badge or authorized key fob or other identification prior to operating the unit. The unit 10 can include an on-board reader that recognizes authorized users via biometrics, magnetic data strips, and the like.

The unit 10 can be configured for pre-defined product data for a particular patient. Thus, the MDI 12A may be electronically identified (e.g., via a bar code label) by the unit 10 before or during installation in the unit 10 or before operation of the unit 10 to help ensure the proper medication is being administered. For example, the unit 10 can include an optical reader that electronically reads a label on the MDI (the MDI may need to be rotated to have the correct orientation before allowing automated dispensing). Other identification devices, such as RFID tags, may be implemented instead of bar codes. The unit 10 may also store information about each MDI drug and about the patient so it can alert the operator to drug incompatibilities or to prevent programming an overdose and generally reduce drug administration errors.

Furthermore, the patient may be identified in a variety of ways prior to administering medication. For example, the unit 10 can be programmatically locked, and the operator must identify the proper patient identification to unlock the unit 10 (e.g., after loading the MDI 12A). That is, the unit 10 may be configured to have a patient-specific code that an operator must use to operate or change the MDIs in the unit 10.

Other methods of automating and controlling the unit 10 are contemplated. For example, the unit 10 may communicate with a wireless handheld device (such as a PDA, cell phone, notepad or smartphone). The handheld device may be used along with or instead of the user interface panel 26 to input parameters such as the number and frequency of doses. A display on the handheld device may display various information along with or instead of the display 28 associated with the unit 10.

Referring to FIG. 5, various of the above operations may be carried out at least in part at modules associated with and/or in communication with the controller 200. For example, operations related to dose counting may be carried out at a dose count module 207, operations related to dose frequency may be carried out at a dosing interval module 210, and operations related to security and safety may be carried out at a security module 211. Other modules can be implemented to carry out these or other operations described herein.

Figure 6:
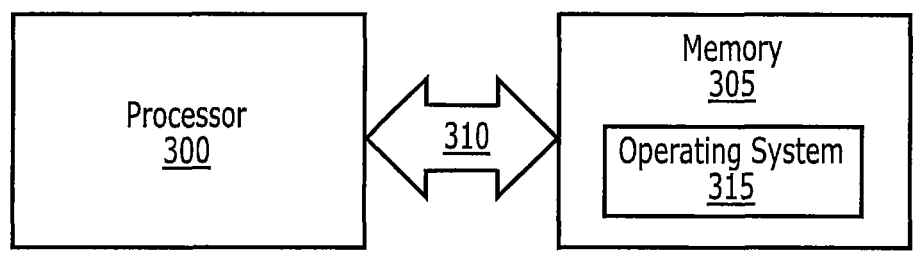
FIG. 6 is a block diagram illustrating a processor and a memory that may be associated with automated medication and control delivery units according to some embodiments.

FIG. 6 illustrates a processor 300 and memory 305 that may be used to carry out at least some of the operations described herein. The controller 200 (FIG. 5) may comprise the processor 300 and/or the memory 305. The processor 300 communicates with the memory 305 via an address/data bus 310. The processor 300 may be, for example, a commercially available or custom microprocessor. The memory 305 is representative of the one or more memory devices containing software and data used to perform operations in accordance with some embodiments of the present invention. The memory 305 may include, but is not limited to, the following types of devices: cache, ROM, PROM, EPROM, EEPROM, flash, SRAM, and DRAM.

As shown in FIG. 6, the memory 305 may contain an operating system 315; the operating system 315 may manage the unit's 10 software and/or hardware resources and may coordinate execution of programs by the processor 300.

Figure 2:
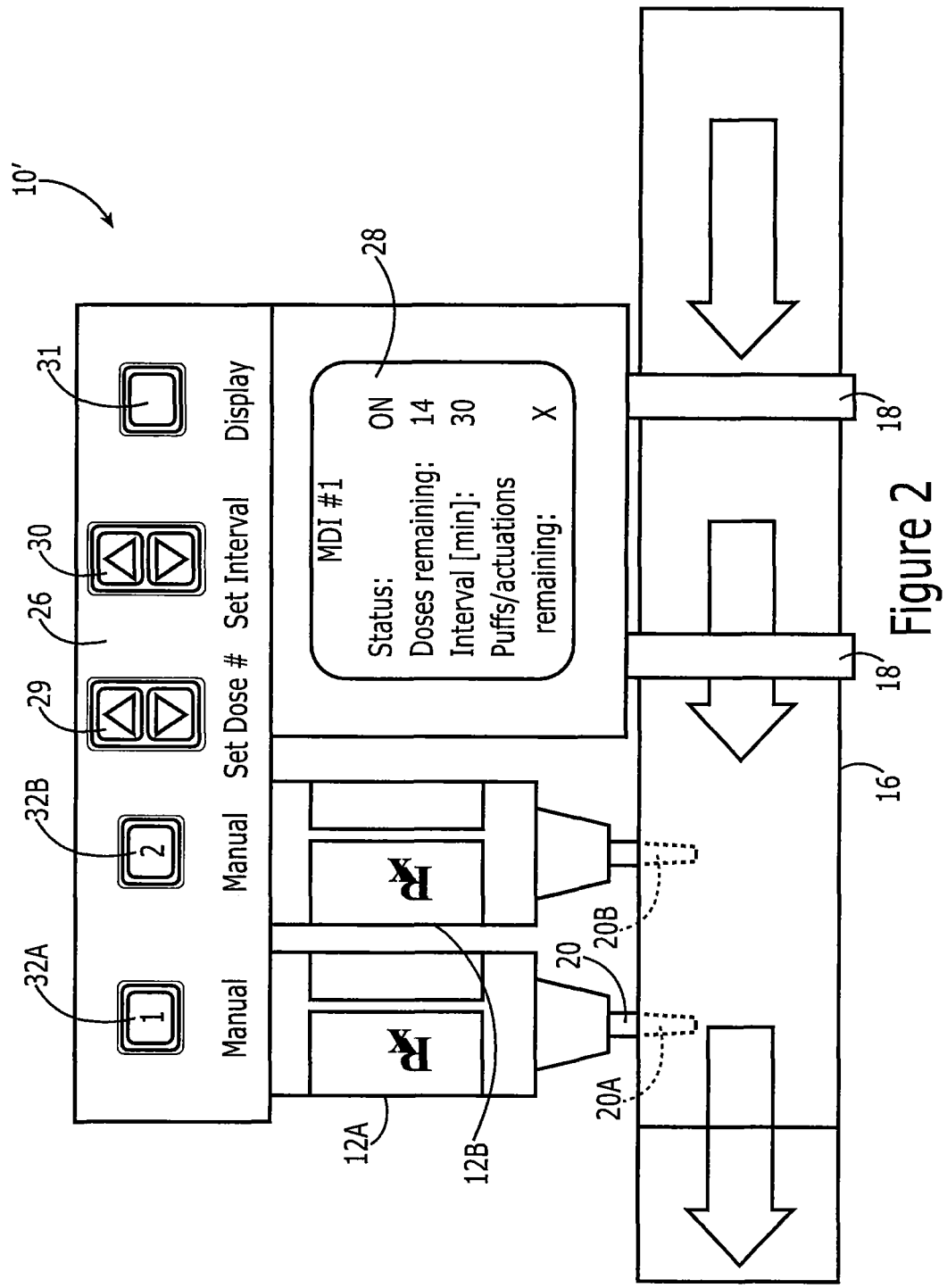
FIG. 2 is a schematic illustration of an alternate automated medication and control delivery unit according to some embodiments.

Another embodiment of an automated control and delivery unit 10' is illustrated in FIG. 2. The unit 10' can include any or all the components and features described above with regard to the unit 10. The unit 10' can be configured to automate the delivery of medication from a plurality of (shown as two) MDIs 12A, 12B. Thus, the unit 10' may include at least a second set of certain components associated with the second MDI 12B. For example, the unit 10' may include two actuators, two agitators, two sets of various sensors, two manual override UI controls 32A, 32B, and the like. Alternatively, the unit 10' can be configured so that each MDI shares certain components (e.g., the agitator, agitator, etc.). Furthermore, the display UI control 31 may allow an operator to toggle between screens to set parameters associated with each of the MDIs 12A, 12B (e.g., the number and frequency of doses, which may be different for each MDI). The operator may also use the display UI control 31 to toggle between screens to view information about each MDI 12A, 12B during automated operation.

It is contemplated that a unit similar to the unit 10' may accommodate more than two MDIs. For example, the additional MDIs may be aligned with the MDIs 12A, 12B shown in FIG. 2. Alternatively, a second housing may extend away from the connector 16 to accommodate additional MDIs. For example, a second housing may be circumferentially and/or axially spaced apart from the unit 10' (e.g., the second housing may reside "beneath" the connector 16 illustrated in FIG. 2). By way of further example, the unit 10' could be rotated by 90 degrees on the vertical axis, and multiple devices could be attached onto a longer connector 16 that has a row of multiple entry ports.

Figure 3:
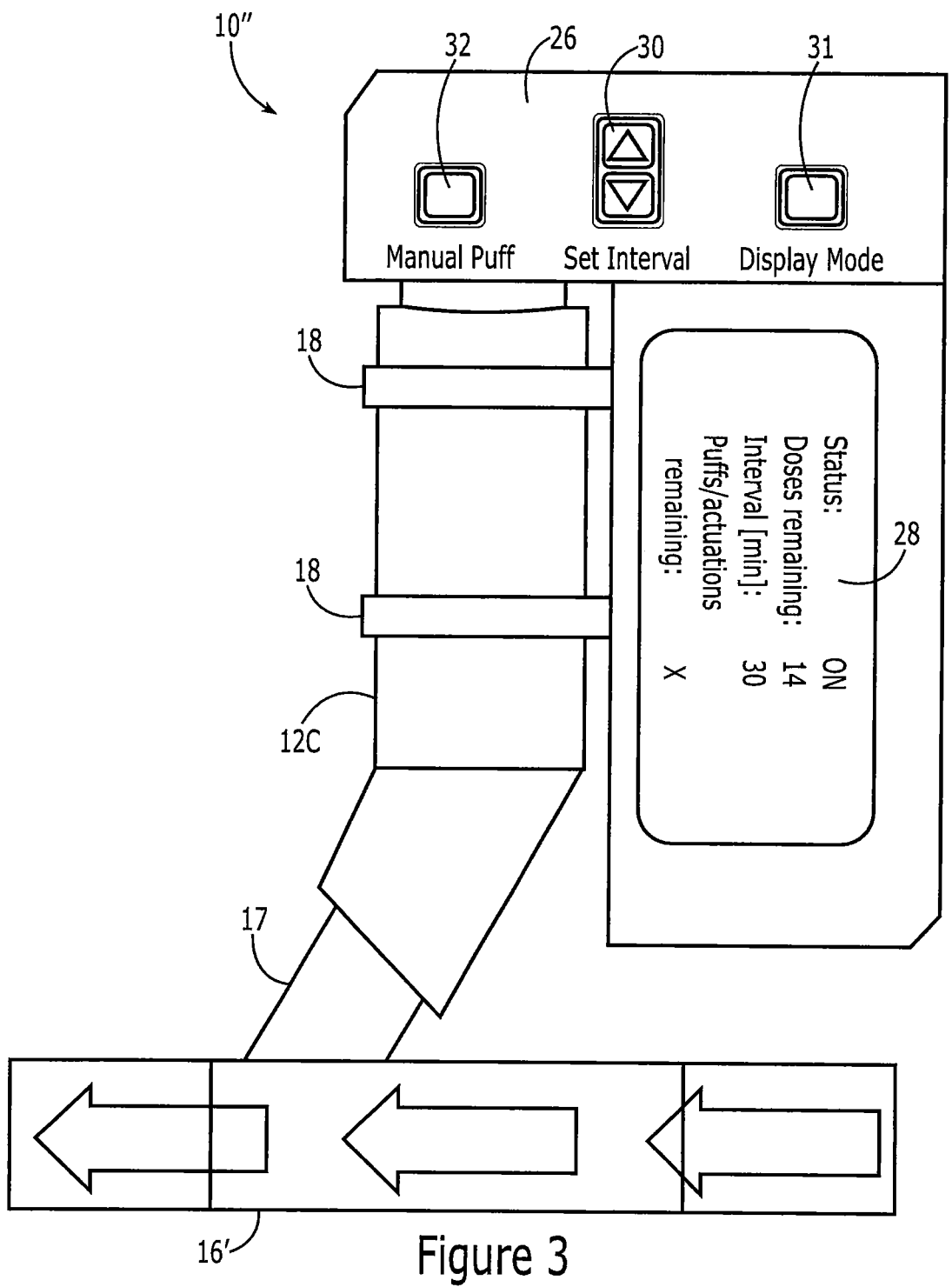
FIG. 3 is a schematic illustration of an alternate automated medication and control delivery unit according to some embodiments.

Another automated control and delivery unit 10" is illustrated in FIG. 3. The unit 10" can include any or all the components and features described above with regard to the units 10, 10'. The unit 10" may be configured such that an off-the-shelf MDI canister 12C (which may be inside a conventional inhaler housing device) can be releasably attached to the unit 10". The MDI 12C may be integrated with a connector 16'. Alternatively, the connector 16' could include segment 17, and the MDI canister 12C could be attached to the segment 17 to communicate with the connector 16'. Holders 18 may releasably secure the MDI 12C and/or the connector 16' to the unit 10". The unit 10" can be used with conventional spacers, adapters and/or MDI canisters. In some embodiments, the unit 10" is a self-supported device.

The units 10, 10', 10" may be used in concert with a heat and moisture exchange (HME) device. HME devices are not always used in ventilator circuits, but their use is well known to those of skill in the art. The designs disclosed herein allow attachment of the MDIs to HME devices.

The units 10, 10', 10" may include a memory, such as the memory 305 (FIG. 6) or other memory, to allow data acquisition capability. In particular, the memory may provide for data capture such that data can be downloaded. The unit can include a USB interface, an Ethernet interface, wireless transmission capabilities, Bluetooth or other connectivity to transmit data to an outside device 215 (FIG. 5). The controller 200 or processor 300 may control the transmission of data from the memory to the outside device 215. The memory may also be provided as a removable memory device, such as a memory stick or the like. The data may then be used for patient records, for assessing the performance of the unit, and for other purposes as would be understood by those of skill in the art.

It is noted that the outside device 215 can be used for other functions, such as entering desired operational parameters, viewing information associated with the unit, receiving alarms, providing security, upgrading software, and other operations described herein. In this regard, the outside device 215 may communicate with the controller 200.

In the embodiments described above, medication from an MDI such as the MDI 12A is typically injected into the ventilator flow circuit 11 via the interior of the connector 16. In some other embodiments, the connector may take a different form, for example the form shown in FIGS. 4A and 4B. As illustrated, the connector 160 includes inner and outer fluid channels 160A, 160B. The channels 160A, 160B are separated by a wall 160W including a plurality of small openings, apertures or perforations 160P. In the illustrated embodiment, the channels 160A, 160B are concentric and the wall 160W takes the form of a cylinder, but other shapes and configurations are envisioned. It is noted that the "ends" of at least the outer channel 160B could be sealed or terminate either at or before the points at which the connector 160 connects with the remainder of the ventilator flow circuit.

Figure 4A:
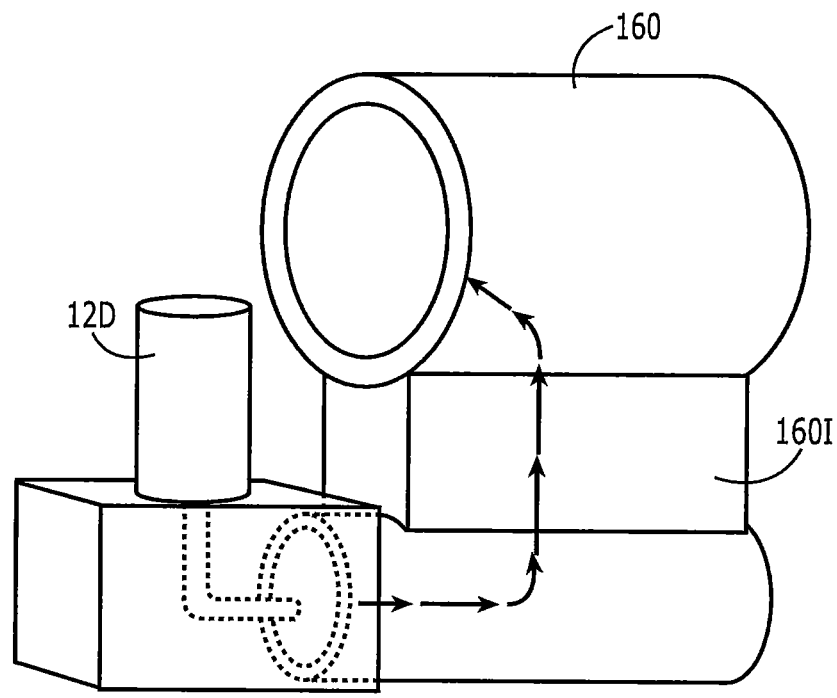
FIGS. 4A and 4B are schematics of a connector for delivering medication to a ventilator circuit according to some embodiments.

In operation, an inhaler 12D is actuated such that medication can be injected into an intermediate passageway 160I of the connector 160, as shown by the dashed arrows in FIG. 4A. The medication then flows into the outer channel 160B, as further shown by the dashed arrows. In some embodiments, the medication can be injected directly into the outer channel 160B. Thus, the medication (usually in the form of a mist or particles) is injected into and, in some embodiments, temporarily "stored" in the intermediate passageway 160I and/or the outer channel 160B. In other words, the intermediate passageway 160I and/or the outer channel 160B can be thought of as a "holding chamber," and the timing to actuate the MDI 12D may not be as critical.

The medication is drawn from the outer channel 160B, through the perforations 160P, and into inner channel 160A, and therefore drawn into the ventilator flow circuit. This may be accomplished via a Venturi effect. In particular, the pressure in the inner channel 160A drops when gas from the ventilator circuit 11 flows therethrough. A pressure gradient between the outer chamber 160B and the inner chamber 160A causes medication particles to be pulled through the perforations 160P and delivered to the patient. The plurality of perforations 160P can help ensure that the medication is evenly dispersed.

Thus, it is envisioned that the release of medication from the MDI 12D is timed so that the medication flows with the gas toward the patient. In some embodiments, the release of medication to the intermediate passageway 160I and/or to the outer channel 160B is timed after the flow of gas from the patient to the ventilator (i.e., after an "exhale").

Other configurations are envisioned. For example, the perforations 160P may be covered during the ventilator cycle except when the flow of gas is toward the patient, at which point they are automatically uncovered. A movable sheath or sleeve can provide the desired open/close configurations. The sheath can rotate or slide axially to perform this function. The sheath can be positioned on the outer surface over the perforations 160P or inside the wall 160W. In other embodiments, a valve may controllably release the medication to the inner chamber 160A only when the proper flow direction is realized. For example, the proper flow (i.e., toward the patient) may actuate the valve and/or uncover the perforations to release the medication. Alternatively, a flow sensor, such as the gas flow sensor 208 described above, may detect the flow direction and/or rate and accordingly the valve may be actuated and/or the perforations may be uncovered responsive to detection by the sensor. In some embodiments, the valve may be positioned between the intermediate passageway 160I and the outer channel 160B, such that medication may be released to the outer channel 160B when the valve opens.

Alternatively or additionally, actuation of the inhaler 12D may be timed based on the flow direction through the inner channel 160A. That is, the gas flow sensor 208 may detect a gas flow in the inner channel 160A or the ventilator circuit 11 that is in the direction from the ventilator to the patient. The sensor 208 may detect that this flow has ceased, or is about to cease, at which point actuation of the inhaler 12D may occur and medication may be delivered into the outer channel 160B and/or the intermediate passageway 160I. In this regard, as the gas flow direction "reverses" to a direction from the ventilator to the patient, the medication may be "staged" for release into the inner channel 160A and the ventilator circuit 11.

Figure 4B:
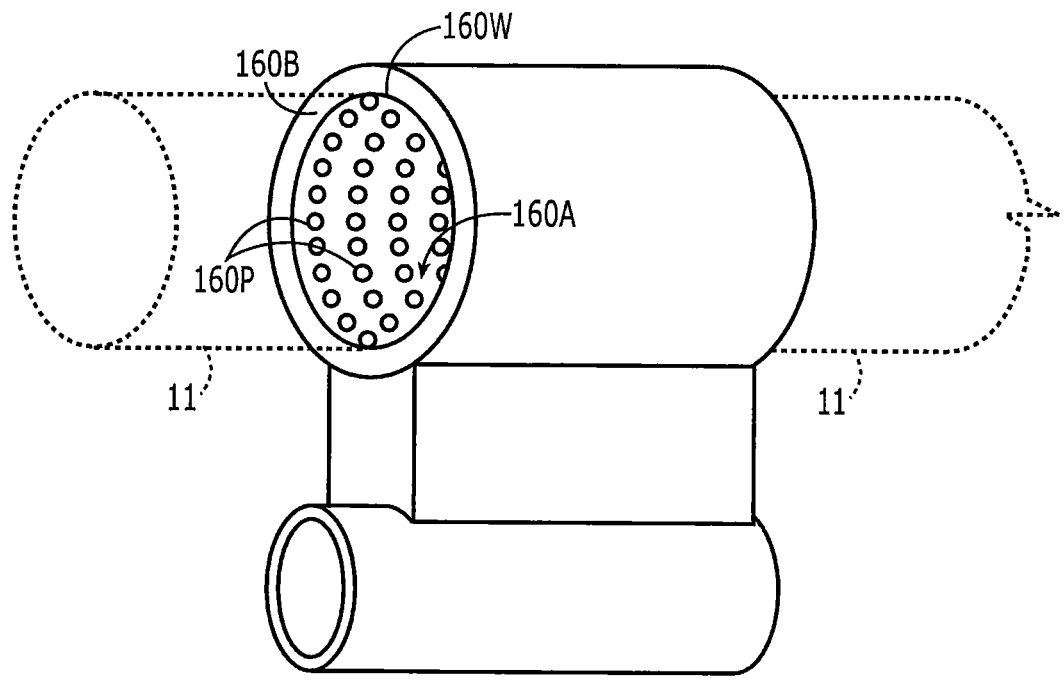

The system shown in FIGS. 4A-4B may be integrated into or operate with the units 10, 10' and 10". Furthermore, any features or components described in reference to FIGS. 4A-4B could be operatively connected to and/or controlled by the controller 200 described above. Thus, the adapter or connector 160 may be used in conjunction with automated delivery units described herein or may simply be used with an inhaler device, such as an MDI.

As described above, the units may include at least one manual override control (e.g., control 32 of the unit 10 illustrated in FIG. 1). This control may allow a caregiver to administer one or more sprays on demand independent of the current or programmed dosing schedule.

In some embodiments, the unit may be designed with the option to allow the patient the ability to self-administer an unscheduled "puff" or dose of medication. For example, referring to FIG. 7, a patient P (such as a mechanical ventilator patient) may have access to a manual override control 132. The manual override control 132 may be attached to or integrated into a hospital bed or may be a device placed within reach of the patient P, such as a control with a depressible button or the like. The control 132 may allow the patient P to self-administer an unscheduled "puff" or dose of medication whenever the patient P senses the need and without having to call a caregiver. This may be useful because mechanical ventilator patients generally cannot easily communicate their needs. For example, this feature may be useful for critical but non-sedated patients.

The manual override control 132 is in communication with unit 10''' such that when the patient P actuates the control 132, the unit 10''' may respond by administering a dose or "puff" of medication. The control 132 and the unit 10''' may be directly electrically coupled (e.g., by a cable or wire) and/or the control 132 may be in wireless communication with the unit 10'''. In particular, a controller 200 of the unit 10''' (FIG. 5) may respond to a signal from the manual override control 132 and then may agitate and/or actuate an MDI to release a puff or dose to the ventilator flow circuit.

The unit 10''' may include both a manual override control for use by a clinician or caregiver (e.g., the control 32 on the unit 10 illustrated in FIG. 1) and the manual override control 132 for use by the patient P. The unit 10''' may include a display with a counter indicating the doses or puffs remaining, and the counter can be decremented when either a patient-initiated or caregiver-initiated manual override is performed.

The unit 10''' may include safety control of patient-initiated drug dispensation within safe parameters as determined by a physician and/or programmed by the unit operator. For example, the unit 10''' may be configured to limit the number of manual overrides that may be performed by the patient P within a given timeframe. The limit can be set based on the medicine and/or the patient. The limit can be programmably adjusted via a local or remote input. The unit 10''' may include a visual indicator (e.g., on a display) and/or may emit an audible signal or alarm each time the patient P uses the manual override or at certain thresholds according to the patient P using the manual override. Moreover, the unit 10''' may include a visual indicator (e.g., on a display) and/or may emit an audible signal or alarm when the patient P is approaching or has reached the programmed limit of manual overrides within a given time period. A display and/or memory associated with the unit 10''' may document the number of patient-initiated manual overrides that have been attempted (and may document the time each override was attempted). The display and/or memory may also document whether medication was dispensed each time the manual override was attempted.

Turning to FIG. 7, a diagnostic device 100 is illustrated. The device 100 may be advantageously used as a driver for early disease detection, reduction of healthcare costs, and/or speedier and/or more effective treatment through personalized care to promote better patient safety and outcome. As will be described below, the device 100 may take the form of one or more of the units 10, 10', 10'', 10''' described herein. Alternatively, the device 100 may be a smaller version and/or may omit certain features of these previously described units. The device 100 may be a standalone unit and may be used in conjunction with one of the units 10, 10', 10'', 10''' described herein.

The device 100 may provide a diagnostic platform and may be used with patients in vivo. The device 100 provides for the administration of inhaled particles, whether they be small chemical agents, small peptide/proteins, whole organisms such as a virus vector, or a radioactive labeled particles (e.g., nucleotide/carbohydrate/gas) that can be thought of as a "drug or pharmaceutical agent." This agent may be used for a clinical effect to measure, diagnose, and/or treat any physiologic process or condition by measuring the exhaled gas to make a physiological reading or measurement to determine a specific state or condition. The device 100 may then use the measured specific state based on the pre-determined/programmed protocol to automatically initiate specified care/treatment (e.g., inhaled antibiotics/inhaled steroids/radioactive gold particles or initiate ventilator weaning) in an automated fashion based on the disease state/condition and/or the physiologic parameter that is chosen to be measured. In various embodiments, the device 100 may be used for only administration purposes, for only detection purposes, and for both administration and detection purposes. In some embodiments, the detected condition or state may be displayed for a clinician or physician; for example, the detected condition or state may be displayed on a display of the device 100. The device 100 may be compact and/or lightweight for the same reasons described above in reference to the unit 10.

Techniques used to diagnose/measure in the device include but are not limited to gas chromatography/capillary GC, liquid chromatography (HPLC/UHPLC), multidimensional chromatography, DNA/RNA sequencing, biophotonic sensors/photometry, biospectroscopy, single cell/multicell flow cytometry, optical microscopy, optical analysis with remote and automated/televised monitoring, mass spectroscopy, IR spectroscopy, antibody labeled ELIZA, gas volatile and non-volatile analysis, small molecule/protein, peptide, carbohydrate hydrocarbon analysis, chemical vapor deposition, calimetry, bioluminensence/luminensence, ion exchange, or any other analytical bio/radio/histochemistry technique that could be used to measure exhaled breath condensate.

Figure 7:
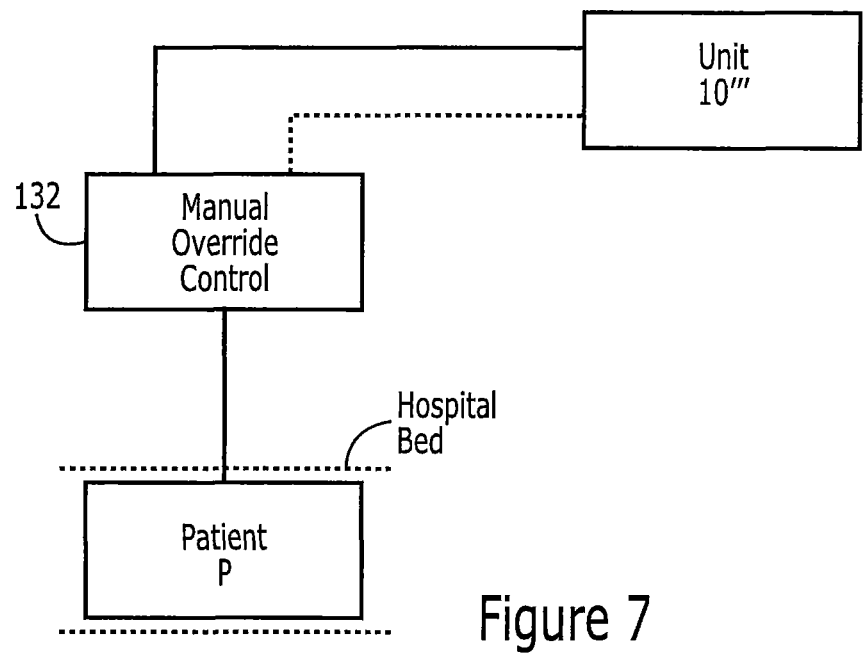
FIG. 7 is a schematic of an automated medication and control delivery unit and a patient-initiated manual control according to some embodiments.
Figure 8:
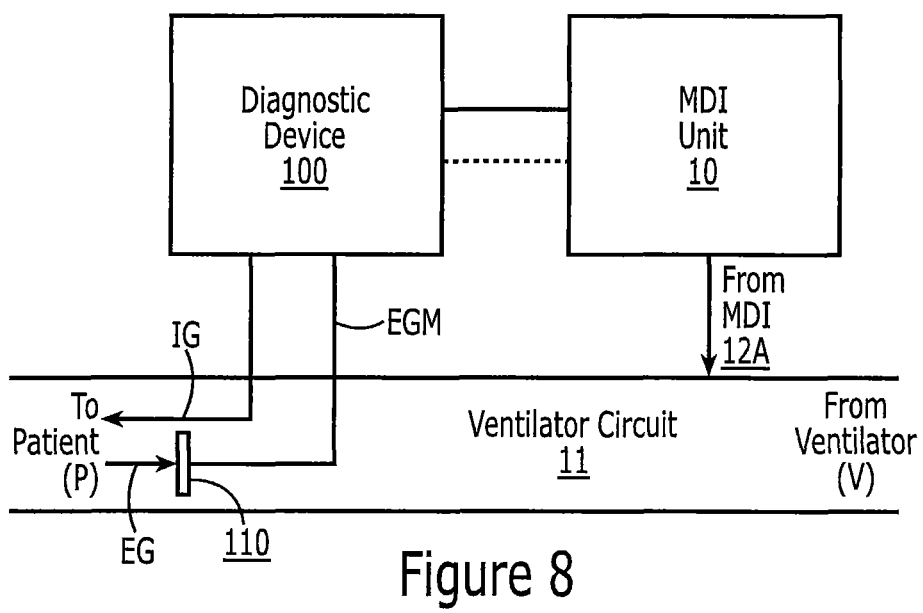
FIG. 8 is a schematic of a diagnostic delivery device or unit, a ventilator circuit and an automated medication and control delivery unit according to some embodiments.

As illustrated in FIG. 7, the device 100 may be a separate or standalone device or unit relative to, for example, the unit 10. The device 100 may inject particles into the ventilator circuit as part of an inhaled gas flow IG. The injection may be timed to occur as the patient is inhaling; for example, this may be accomplished using the gas flow sensor (FIG. 5). After the patient has inhaled the particles and then exhaled, an exhaled gas flow EG may be measured using an exhaled gas measurement sensor 110. The exhaled gas measurement sensor 110 is positioned in the ventilator circuit and may be disposed between the patient and the diagnostic device 100. The exhaled gas measurement sensor 110 measures exhaled breath condensate using one or more of the techniques described above. For example, the amount or concentration of exhaled "waste gas" could be measured after the particles have been administered.

A physiological reading or measurement (or exhaled gas measurement EGM) is communicated from the sensor 110 to the device 100. The EGM may be communicated to a controller within the device 100 or may also be communicated to an outside device for further processing. The controller or outside device determines a specific state or condition of the patient based on the EGM. The controller may then adjust a medication dosing or timing based on the specific state or condition of the patient. The device 100 may include a display (not shown) which may display parameters related to the determined specific state or condition of the patient and/or the current medication dosing or frequency and/or any adjustment thereto.

As illustrated in FIG. 7, the device 100 may be in communication with the automated medication and control delivery unit 10. The device 100 may communicate the specific state or condition of the patient to the MDI unit 10 (or to the controller of the unit 10) such that dosing or timing of dosing may be adjusted from the unit 10. Alternatively, the exhaled gas measurement EGM may be communicated directly to the unit 10 or controller therein for processing to determine the specific state or condition of the patient, at which point the unit 10 may adjust the dosing or frequency of dosing accordingly. The display 28 on the unit 10 (FIG. 1) may display parameters related to the determined specific state or condition of the patient and/or the current medication dosing or frequency and/or any adjustment thereto.

It is also contemplated that the diagnostic device 100 could be integrated with an automated medication and control delivery unit as a single unit or device. That is, the device 100 (or some or all of its features) may be integrated with any of the units 10, 10', 10", 10'" described herein. By way of example, referring to FIG. 2, one of the inhalers 12A, 12B of the unit 10' may take the form of a container containing the diagnostic particles described above for injection as part of the inhaled gas. The subsequently exhaled gas, may be measured using a sensor in the ventilator circuit and the exhaled gas measurement may be communicated to the controller of the unit 10'. The specific state or condition of the patient may be determined by the controller in response to the exhaled gas measurement and the controller may then regulate or control the medication dosage or frequency from the other of the inhalers 12A, 12B responsive to the determined specific state or condition.

The foregoing is illustrative of the present invention, and is not to be construed as limiting thereof. Although exemplary embodiments of this invention have been described, those skilled in the art will readily appreciate that many modifications are possible in the exemplary embodiments without materially departing from the novel teachings and advantages of this invention. As such, all such modifications are intended to be included within the scope of this invention. The scope of the invention is to be defined by the following claims.

That which is claimed is:

1. A system for providing automated delivery of medication to a ventilator circuit that extends between a mechanical ventilator and a patient, the system comprising:
   a connector that resides in-line with a portion of the ventilator circuit;
   a portable medication delivery unit attached to the connector, the portable delivery unit comprising:
      a housing releasably holding an upper end portion of at least one metered dose inhaler (MDI) canister containing medication such that a major portion of the canister extends outside the housing, wherein the canister includes an outlet nozzle residing below and opposite the upper end portion that is received through an entry port in the connector such that the canister is in fluid communication with the ventilator circuit; and
      an actuator held by the housing and in communication with the canister to direct the canister to release medication to the ventilator circuit for the patient, wherein the actuator is disposed adjacent the upper end portion of the canister; and
   a control device in communication with the portable delivery unit, the control device configured to control an amount and/or frequency of medication delivery from the canister to the ventilator circuit for a respective patient and to direct the actuator to actuate and deliver the medication from the canister to the ventilator circuit at a defined amount and/or frequency.

2. The system of claim 1, wherein the portable delivery unit is releasably attached to the connector such that the housing is adjacent and/or on the connector with the connector extending completely outside the housing.

3. The system of claim 1, wherein the portable delivery unit is a compact, lightweight device.

4. The system of claim 1, wherein the control device comprises a user interface to allow an operator to input to the control device the amount and/or frequency of medication delivery from the canister to the ventilator circuit for the patient.

5. The system of claim 4, wherein the user interface comprises a manual override control to direct the actuator to actuate to deliver medication from the canister to the ventilator circuit for a respective patient irrespective of the defined amount and/or frequency of medication delivery.

6. The system of claim 1, wherein the control device comprises a display for displaying parameters including the defined amount and/or frequency of medication delivery and an amount of medication remaining in the canister, wherein the control device is configured to dynamically update the displayed parameters.

7. The system of claim 1, wherein the control device is a handheld electronic device.

8. The system of claim 7, wherein the control device is in wireless communication with the delivery unit.

9. The system of claim 1, further comprising a gas flow sensor disposed in the interior of the connector, the gas flow sensor configured to detect a gas flow direction through the connector and communicate the gas flow direction to the control device.

10. The system of claim 9, wherein the control device is configured to direct the actuator to actuate to deliver medication from the canister to the ventilator circuit when the gas flow direction in the connector is from the ventilator to the patient based on data detected by the gas flow sensor.

11. The system of claim 9, wherein the gas flow sensor is configured to detect at least one gas flow characteristic of gas flowing through the connector and to communicate the detected at least one gas flow characteristic to the control device, and wherein the control device is configured to adjust the amount and/or frequency of medication delivery in response to the detected at least one gas flow characteristic.

12. The system of claim 1, further comprising a gas flow sensor disposed in the ventilator circuit, the gas flow sensor configured to detect a gas flow direction through the ventilator circuit and communicate the gas flow direction to the control device, wherein the control device is configured to direct the actuator to actuate and deliver medication from the canister to the ventilator circuit in response to the gas flow sensor detecting a gas flow direction from the ventilator to the patient.

13. The system of claim 1, wherein the control device is configured to:
  (i) lock the unit to prevent actuation of the actuator and prevent unwanted adjustment of operational parameters;
  (ii) receive identification information associated with an operator of the unit;
  (iii) verify that the operator is an authorized user based on the identification information; and
  (iv) unlock the unit and direct the actuator to actuate and deliver medication from the canister to the ventilator circuit in response to verification that the operator is an authorized user.

14. The system of claim 1, wherein the control device is configured to:
  (i) lock the unit to prevent actuation of the actuator and prevent unwanted adjustment of operational parameters;
  (ii) receive identification information associated with a patient;
  (iii) verify that the patient is to receive the medication contained in the canister based on the identification information; and
  (iv) unlock the unit and direct the actuator to actuate and deliver medication from the canister to the ventilator circuit in response to verification that the patient is to receive the medication contained in the canister.

15. The system of claim 1, wherein the control device is configured to:
  (i) lock the unit to prevent actuation of the actuator and prevent unwanted adjustment of operational parameters;
  (ii) receive identification information associated with the patient;
  (iii) electronically identify the canister that is held by the housing;
  (iv) verify that the patient is to receive the medication contained in the canister based on the identification information associated with the patient and the electronic identification of the canister; and
  (v) unlock the unit and direct the actuator to actuate and deliver medication from the canister to the ventilator circuit in response to verification that the patient is to receive the medication contained in the inhaler.

16. The system of claim 1, wherein the delivery unit is releasably attached to the connector by at least one holding member that holds the housing in place.

17. The system of claim 1, wherein the delivery unit comprises an identification device configured to electronically identify the canister held by the housing.

* * * * *